(12) United States Patent
Riesinger

(10) Patent No.: US 8,603,053 B2
(45) Date of Patent: Dec. 10, 2013

(54) PRIMARY DRESSING

(76) Inventor: Birgit Riesinger, Ostbevern (DE)

( * ) Notice: Subject to any disclaimer, the term of this patent is extended or adjusted under 35 U.S.C. 154(b) by 315 days.

(21) Appl. No.: 12/226,109

(22) PCT Filed: Apr. 11, 2007

(86) PCT No.: PCT/EP2007/003214
§ 371 (c)(1),
(2), (4) Date: Nov. 24, 2008

(87) PCT Pub. No.: WO2007/118652
PCT Pub. Date: Oct. 25, 2007

(65) Prior Publication Data
US 2009/0093779 A1 Apr. 9, 2009

(30) Foreign Application Priority Data

Apr. 12, 2006 (DE) .......................... 10 2006 017 194

(51) Int. Cl.
*A61F 13/00* (2006.01)
(52) U.S. Cl.
USPC .............. 604/304; 604/307; 604/383; 602/47
(58) Field of Classification Search
USPC ............. 604/290, 304, 307–308, 383; 602/47
See application file for complete search history.

(56) References Cited

U.S. PATENT DOCUMENTS

| 3,054,148 | A | | 9/1962 | Zimmerli |
| 5,078,710 | A | * | 1/1992 | Suda et al. ..................... 604/383 |
| 5,620,771 | A | | 4/1997 | Middleton |
| 5,762,643 | A | * | 6/1998 | Ray et al. ....................... 604/383 |
| 5,897,543 | A | * | 4/1999 | Francis .......................... 604/383 |
| 6,255,552 | B1 | | 7/2001 | Cummings et al. ............. 602/58 |
| 6,566,577 | B1 | | 5/2003 | Addison et al. ................. 602/56 |
| 6,627,791 | B1 | * | 9/2003 | Veglio et al. ................... 604/383 |
| 2002/0115972 | A1 | * | 8/2002 | Dabi et al. ..................... 604/383 |
| 2002/0133132 | A1 | * | 9/2002 | Copat et al. .................... 604/383 |

FOREIGN PATENT DOCUMENTS

| DE | 20 2004 017 052 U1 | 7/2005 |
| DE | 202004017052 U1 | 7/2005 |
| DE | 202004017465 U1 | 1/2006 |
| EP | 0 081 988 A1 | 6/1983 |

(Continued)

OTHER PUBLICATIONS

McAirlaid's Vliesstoffe GmBH & Co. KG, "Notice of Opposition to a European Patent", filed by Christophersen & Partner, Patentanwaelte, filed on Mar. 9, 2012, p. 1-15.

Paul Hartman AG, "Notice of Opposition to a European Patent", filed by Dreiss Patentanwäite Partnerschaft, filed on Mar. 13, 2012, p. 1-19.

Protz, K., "Moderne Wunauflagen unterstützen Heilungsprozess", *Geriatri Journal*, p. 3333-3339, (Apr. 2005).

(Continued)

*Primary Examiner* — Lynne Anderson
(74) *Attorney, Agent, or Firm* — J. Peter Paredes; Rosenbaum IP

(57) ABSTRACT

The invention relates to a liquid-permeable primary dressing in the form of a supple thermoplastic section of material (1.4), comprising: a first smooth surface (4); a second surface (5) facing away from the smooth surface (4); and a plurality of three-dimensional perforations, whose walls extend from the first smooth surface (4) and end in an overhang with a free edge, thus making the second surface (5) rough to the touch. At least one of the free edges has an angled section that is approximately perpendicular to a perforation axis. In a preferred embodiment, the periphery (13) of the material section is smooth on both sides, i.e. on both the first and second surfaces (4; 5), the periphery (13) of the surface (5) that was at first rough being thermally smoothed.

18 Claims, 6 Drawing Sheets

(56) References Cited

FOREIGN PATENT DOCUMENTS

| EP | 0 302 611 A1 | 2/1989 |
| EP | 0 934 736 A1 | 8/1999 |
| EP | 1500384 | 1/2005 |
| WO | WO 96-20664 | 7/1996 |
| WO | 97/03795 | 2/1997 |
| WO | 00/16726 | 3/2000 |
| WO | 00/59436 | 10/2000 |

OTHER PUBLICATIONS

Quelette, WR., "Formed Films—The 'Hole' Story", *Nonwovens World*, p. 69, 72 & 73, (May/Jun. 1986).
Wallenfang, K., et al., "Wound Management with Currently Available Wound Dressing for Phase Adapted Treatment", *AKT Dermatol*, vol. 27, p. 343-350, (2001).
Waller, P., "Declaration by Inventor", p. 1-2, (Oct. 20, 2011).
Enhanced section of an image that focuses in on a three dimensional perforation in a thermoplastic material.

* cited by examiner

PRIMARY DRESSING

The invention relates to a liquid-permeable primary dressing in the form of a flexible thermoplastic material section comprising:
a first smooth surface,
a second surface of the material section facing away from the smooth surface,
a plurality of three-dimensional perforations whose walls, starting from the first smooth surface, run out into an edge projection with a free edge and impart a rough grip to the second surface.

Such liquid-permeable, thermoplastic material sections are used as so-called top sheets in the hygiene field, primarily in feminine hygiene, a hospital supports or in baby diapers. A perforated foil material can be gathered from U.S. Pat. No. 3,054,148 that comprises a plurality of three-dimensionally designed perforations. The perforations are produced with the aid of a perforated sieve arranged on a drum in the thermally supported vacuum process. Accordingly, the finished foil material has a smooth surface and a rough surface formed by the bent walls of the perforations.

Furthermore, EP 0 081 988 B1 teaches a primary dressing that also comprises perforations. No details regarding surface quality of the material section forming the primary dressing can be gathered from the document. No rough and no smooth surface was described. The periphery of the primary dressing is free of perforations. Such a design of the primary dressing is expensive. Moreover, a secondary dressing (wound pillow) is connected via a further adhesive layer in a sandwich-like manner to the primary dressing.

The invention has the problem of expanding the range of use of the material sections of the initially cited type around the wound treatment. In particular, the material section for covering the wound should function as the primary dressing onto which the absorbent secondary dressings can be placed without adhesive and should counteract the sticky areas and adhesions with the wound exudate. A wound contact grid should be available that rests on the wound in an almost ideal punctiform manner, is hypoallergenic and economical that can be connected to a replaceable absorption body that is added in subsequently, and that guarantees the passage of wound fluids even under pressure due to a selected surface relationship between material and gap. The foil material determines an orientation into a smooth surface corresponding to the sensitive wound and a rough side bag the selection of the funnel-shaped material deflections.

A primary dressing in accordance with the invention that functions as wound covering avoiding sticky areas and adhesions with the wound exudate, on which dressing at least one absorbent secondary dressing can be placed, comprises:
a flexible material section consisting of a thermoplastic, which material section comprises a first smooth surface and the second surface facing away from the smooth surface and at a distance from it,
a plurality of three-dimensional perforations whose walls run out, starting from the first smooth surface, into an edge projection with the free edge and impart a rough grip to the second surface, and at least one of the free edges merges into a section bent approximately vertically to a perforation axis (A).

The substantially conically designed walls of the perforations should be small enough for a through meniscus formation of liquids with specific weights between 0.9 and 1.2. The specific weight of 0.9 to 1.2 corresponds to the liquid wound exudate. In the present case the concept of meniscus denotes a convex or concave surface of the wound liquid moving in a capillary manner that goes back to the interaction of the wound liquid with the surfaces of the primary dressing and of the particular wound.

The bent section on the rough surface bring about a desirable reduction of the reflux of wound fluids that have already occurred.

The material section should be understood as an additive to a wound dressing that is used in direct contact with the wound and due to its three-dimensional form does not have contact with the wound over its entire surface, which additive has no absorbing function or apparatus but rather on the contrary should be combined in a replaceable manner with other products functioning as secondary dressing. It thus forms a primary dressing in the sense of the invention. The additive and/or the primary dressing should be used for acute and chronic wounds, iatrogenic separations of the skin, burn wounds, wetting, inflamed processes of the skin or exulcerating processes of neoplastic genesis, wetting infections, fistulas, postoperative drainages, stomata, atopically changeable areas of the skin, skin folds in the vicinity of articulations such as armpit skin or inguinal skin, mucus membrane surfaces of man and of animal as well as in combination with other dressing substances that have local therapeutic effect and in other applications in which an atraumatic wound covering is indicated.

The production of a three-dimensional foil of the type to be described here requires, in accordance with the cited goals, the creation of a smooth and of a rough surface which two surfaces can have a property that furthers wound healing. The smooth surface protects the wound from irritation and undesirable influences of the secondary dressing whereas the rough surface also does this but on the other hand actively rubs on the wound during movement and thus can signify a desired chemotactic stimulation for the formation of new tissue.

The surface of the material section is preferably formed straight and plane and the perforations or holes can be delimited by scrap-like material deflections. The craters, funnels or even feet produced preferably have the same depth so that a contact surface is produced that can consist solely of the edges, facing away from the former surface, of the sections that were formerly plane but are now deflected up to 30 to 179 degrees.

The perforations themselves can be polygonal, round, oval, triangular or multi-cornered or also have no given structure; however, they preferably form streets of homogenous hole geometries.

Remainders that are also plane and conditioned by the manufacture can be located on the edges of the craters facing away from the former surface, which remainders were not stamped out of only partially stamped out. However, the goal can also be to form the ends of the funnels without a second or even a first incomplete deflection into the remainders running approximately parallel to the plane surface in such a manner that a grid structure is striven for that is plane in its entirety but with repeating craters with the same depth projecting at approximately right angles in only one direction.

Embodiments are also conceivable that comprise small-area, plane material sections running parallel to the flat side on the lower delimitation of the funnels which material sections are produced, for example, in that the holes are purposefully not completely stamped out. These section contribute, in spite of their possibly only small surface, to the fact that absorbed wound exudate can flow back only with difficulty in the direction of the wound. This effect is produced substantially by the alignment of the funnels and craters but can be supported by these surfaces.

The material section should be hard enough to ensure the tear resistance, especially on account of the perforations present, but on the other hand should be soft enough to avoid brittleness and to create flexibility.

It can be appropriate to strive for different geometry. The combination of round and oblong perforations is conceivable since as a result thereof additional reliability is gained for achieving areal passage areas even under pressure.

The street-shaped alignment of the perforations can be appropriate for avoiding inhomogeneous differences of elasticity. This street-shaped alignment can have the result that direction-dependent differences in the tear resistance are produced so that the material section can have a greater or lesser strength transversally to the street.

Inside the street the localization of the holes can take place in a staggered manner so that an accordion-like placing of round perforations can be framed in by streets of oblong holes.

Polyethylene can be considered as material, in particular UV-unstable PE with very low density (ULDPE, ultra-density polyethylene); however, even other plastics, natural substances or compounds for both types can be selected. They can be carrier substances for pharmaceutical products such as, e.g., antibiotics, growth factors, inflammation inhibitors (NSAID, steroids or other groups). They can be (in)directly connected to carboxy methylcellulose, metallic particles, in particular nanometals, mixtures with honey and its derivatives, aloe vera, hydrofibers, disinfectants, hydrogels, enzymes, fats, vitamins, minerals, collagen, antibiotics, super-absorbing granulates or similar local therapeutic agents. It is also conceivable in combination with the wound distancing grid, that the super-absorbing granulates are present like a depot impregnated with solutions of pharmaceutical agents so that the active substances can be applied via a continuous administration into the wound region; depending on the resorption, a systemically acting application would also be conceivable via this mechanism.

For example, cotton or silk provided with a hydrophobic agent can be used as natural substance. An artificial silk or spider silk is also conceivable.

The flexible foil material can be removed without residue after having been placed possibly for several days on the wound. Since it then had been placed alone at first in order to subsequently distance secondary dressing from the wound that had possibly been replaced several times due to rather strong exudation, it had possibly been successively provided in time with several absorption bodies.

The foil material can comprise a coating that further reduces its adhesion. Coating processes of various types are already widely found in the state of the art for foil production. This coating preferably does not influence the flexibility of the product since the foil material should adapt almost parallel to the wound surface. It can be desirable here that at least parts of the material section lie on healthy skin sincere they project past the wound surface. Teflon, fats, siliconized additives or additives provided with hydrocolloids are available.

It can also be provided that the primary dressing is folded in an orderly manner or chaotically in order to be used in the form of a wound filler or in tunnel-forming envelopes under the skin.

Purely geometrically, the edges of the perforations form the material parts of the wound distancing grid that are the furthest removed from the wound surface when the smooth side faces the wound surface. This application is used most often, compared to the application of the rough side on the wound, because this determines its property of being able to be detached from the wound surface in the sense of an atraumatic wound coating without resulting in bleeding, pain or detachment processes from adhered surfaces.

The primary dressing, called the wound distancing grid in the following, rests lying on its flat side either on the plane areas between the holes of the smooth surface or on the rough delimitations of the perforations since the transition from the grid material to the holes determines the contact area of the rough surface. Thus, this wound distancing grid can have wound contact in two orientations with two very different functions.

The use of this wound distancing grid results in keeping clean micro-perforated surfaces of the second dressing since coarse contamination such as fibrin coatings, scabs or putrid processes cannot pass directly into the outer casing of the secondarily applied absorption body but rather remain at the bottom of the wound without clogging the pores of the secondary dressing. By means of this effect the wound distancing grid maintains the function of the secondary dressing in the case of contaminated wounds and prolongs its application time or makes possible the assumption of its function since the above-cited contaminations remain on the areas of the wound distancing grid without displacing the holes.

The number of round holes can be greater than that of the oval holes, preferably two times greater. The diameter of the spheroidal holes is preferably 650 to 800 µm and the length of the oblong holes is preferably 900 to 1200 µm at a width of approximately 700 µm. The holes preferably form 25% of the total area in a top view onto the flat side of the wound distancing grid.

The primary dressing can find its preferred usage in compression therapies of chronic wounds such as, e.g., Ulcus cruris or, however, vacuum therapy, in which elements of the dressing are pressed into the wound region under the production of subatmospheric pressure conditions.

It is appropriate for the use as wound distancing grid to sterilize the product and to place it into a likewise sterilized, bag-like packaging.

The invention will be described in the following using the drawings.

FIG. 2 shows a section A-A according to FIG. 1a;

FIG. 1 shows a primary dressing 100 in the form of a rectangular flexible material section 1.1 of UV-unstable polyethylene with a very slight thickness. The thickness is in the present case between 0.890 g/cm$^3$ and 0.915 g/cm$^3$.

Figure 1A:
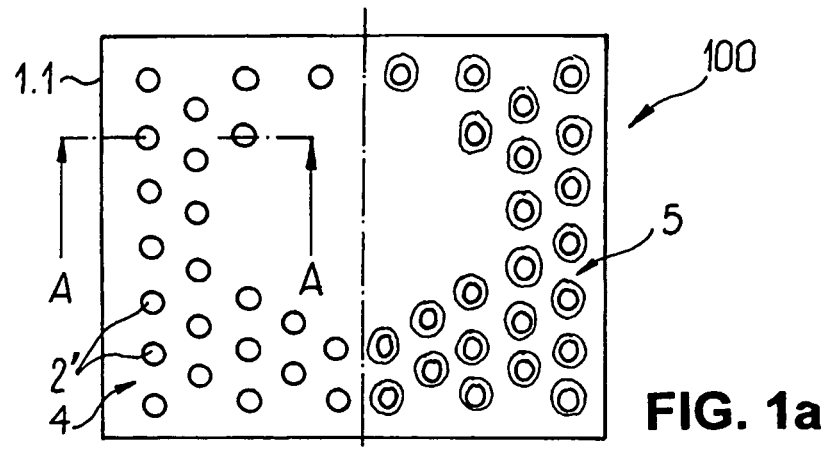
FIGS. 1a, 1b, 1c show a wound distancing grid with round and oval or oblong perforations in a top view onto its smooth and rough surface.

The left side of FIG. 1a shows a smooth surface 4 and the right side shows a rough surface 5 of material section 1.

The concept "material section" will be replaced in the following by "wound distancing grid".

Figure 2:
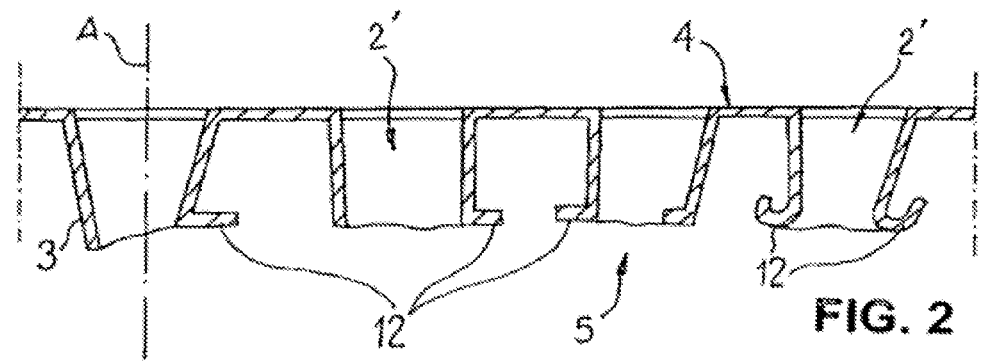

The wound distancing grid 1.1 comprises a plurality of round perforations 2' comprising conically formed walls 3 according to FIG. 2 which both again run out in an irregular manner in scrap-like sections 12 aligned approximately vertical to a perforation axis A. Sections 12 can also be folded inward or outward, as the right side of FIG. 2 shows. This can take place by using a warm current of air, e.g., with the aid of a warm air nozzle, a hair dryer or the like. The described construction of perforations 2' contributes to the fact that the absorbed wound exudate can flow back in the direction of the wound only with difficulty.

Figure 1B:
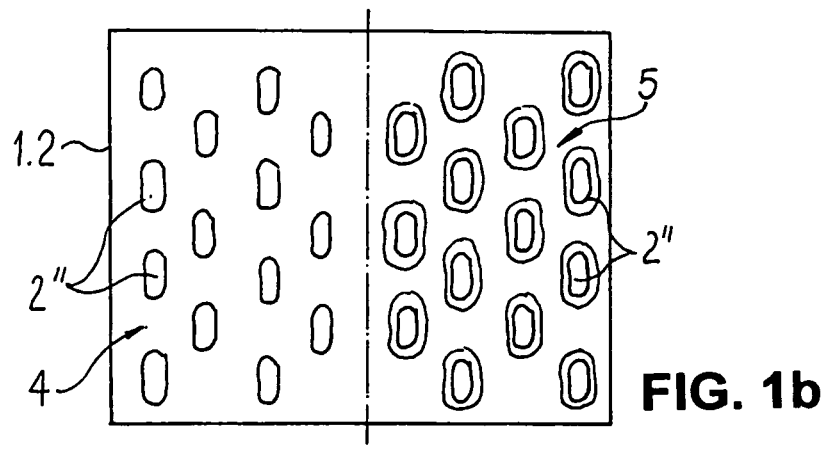

The primary dressing shown in FIG. 1b is a similar wound distancing grid 1.2 comprising a plurality of oval perforations 2".

Figure 1C:
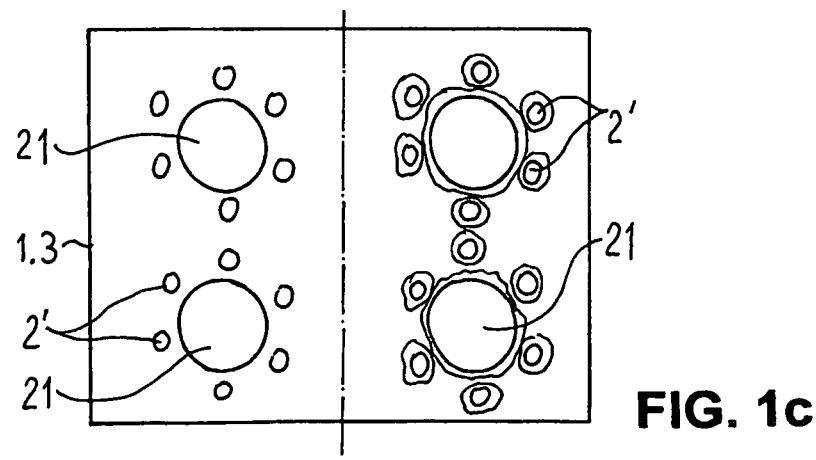

According to FIG. 1c oval perforations 21 are formed on wound distancing grid 1.3 that likewise merge into bent walls 3 and are surrounded by a plurality of round perforations 2'. In the present case six round perforations are formed around hole 21 but their number can be as desired.

Figure 12:
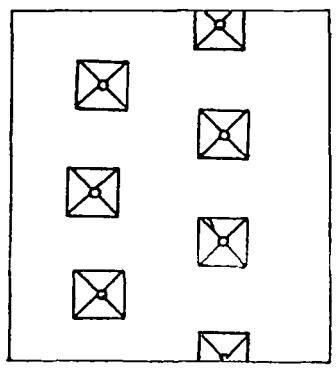
FIGS. 12 to 14 show the rough surface of the wound distancing grid with pyramidal perforations.
Figure 13:
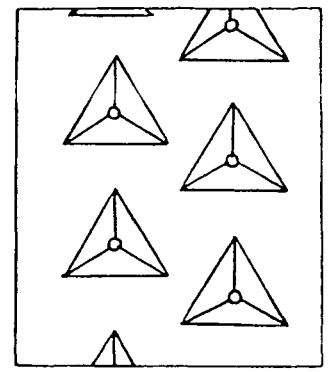
Figure 14:
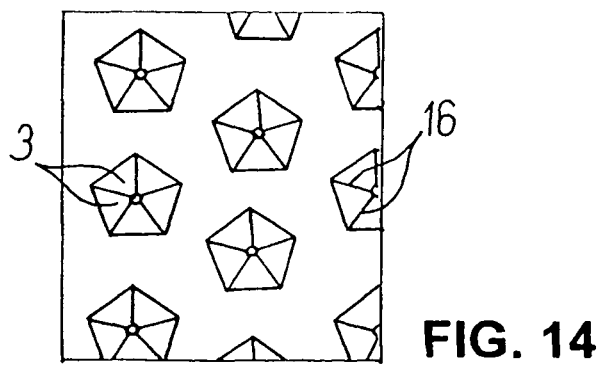

According to FIGS. 12, 13 and 14 the perforations are present in triangular, rectangular and pentagonal pyramidal forms. The walls of the pyramids are segmented, i.e., separated from each other with stamped lines 16.

Figure 3A:
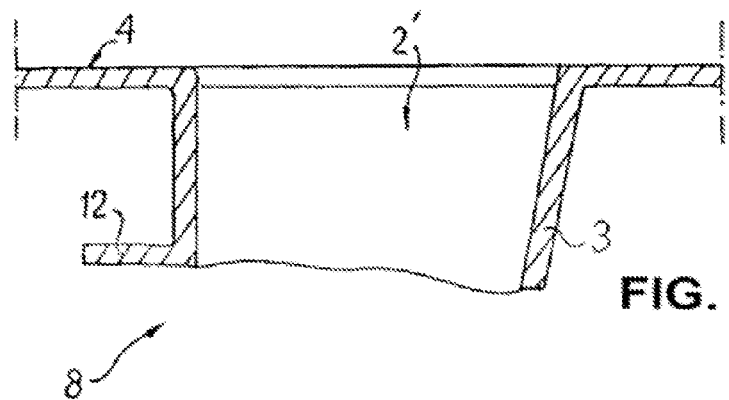
FIGS. 3a, 3b show a conical perforation in a greatly enlarged view.
Figure 3B:
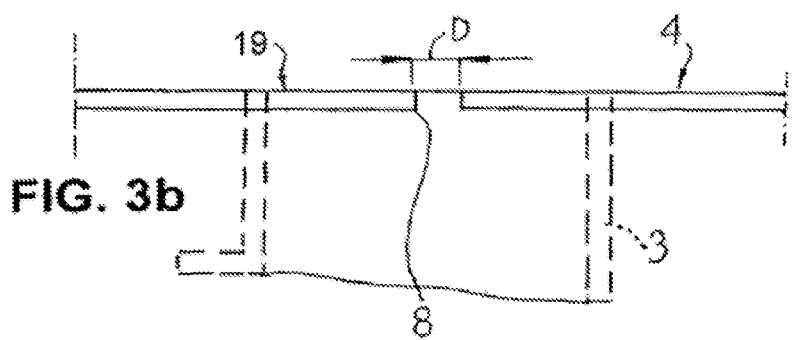

FIG. 3a shows an enlarged detail of perforation 2' with conically running wall 3 and with an outwardly projecting section 12. After the smoothing out of the perforation, e.g., with the aid of a tool like an iron under the supplying of heat, a plane area 19 results (see FIG. 3b), in which the perforation does not disappear but rather is reduced to an opening with a diameter D shown in the figure that is substantially smaller than the original perforation 2'.

Figure 4:
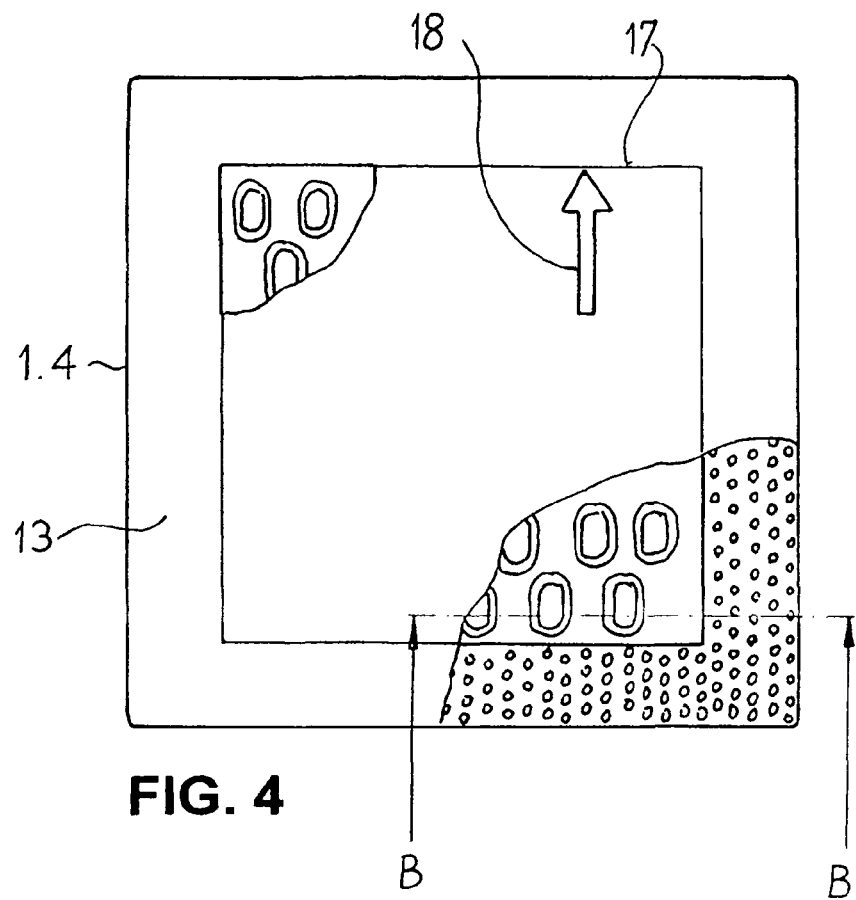
FIG. 4 shows another embodiment of the wound distancing grid in a top view onto its bottom.
Figure 5:
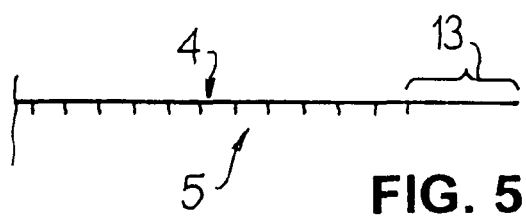
FIG. 5 shows a section B-B according to FIG. 4.

This smoothing of three-dimensional perforations to a plane area is now utilized in order to achieve a periphery 13 smooth on both sides on a wound distancing grid 1.4 shown in FIGS. 4 and 5. A circumferential marking 17 added on the wound distancing grid optically delimits the middle field, that is, the raw surface 5 of smooth periphery 13. Another marking 18 in an arrow form shows the tear-resistant direction.

Figure 10:
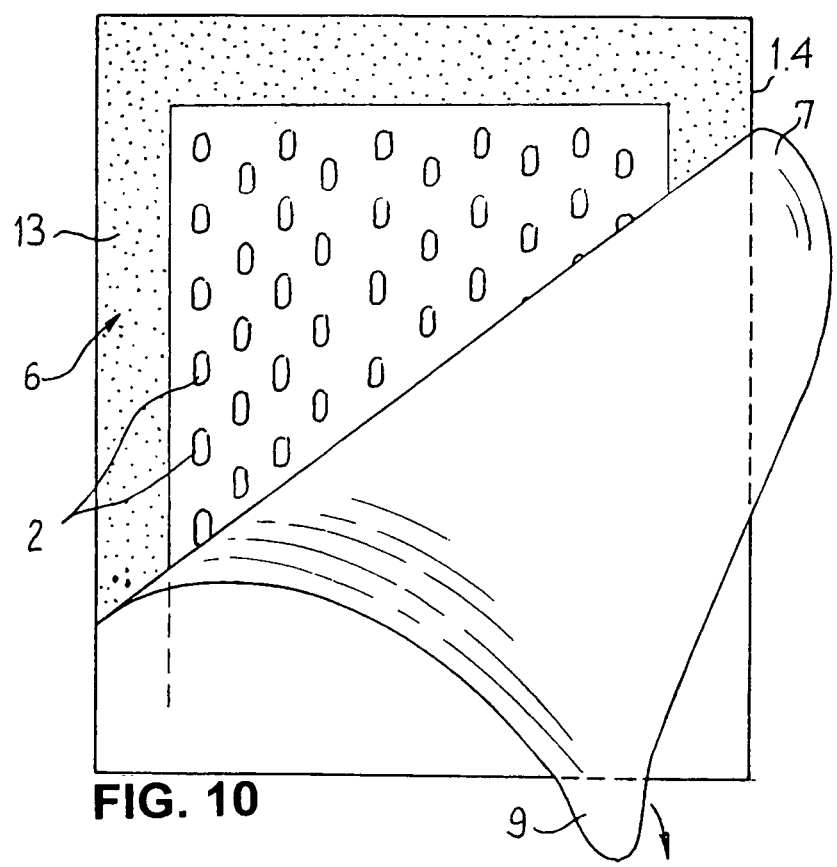
FIG. 10 shows a wound distancing grid according to FIG. 4 with pull-off foil.

FIG. 10 also shows wound distancing grid 1.4 but with a peripheral adhesive area 6 that coincides with smooth periphery 13. Adhesive area 6 is provided with a pull-off protective foil 7 with pull-off flap 9.

Figure 6:
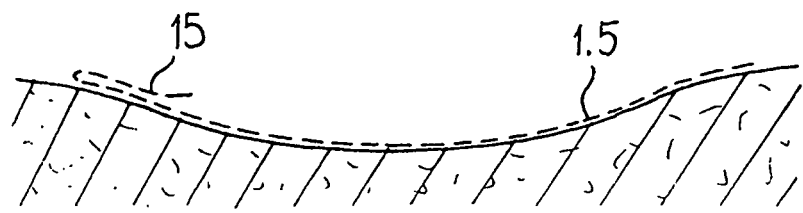
FIG. 6 shows a wound distancing grid with a turned-back fold placed on a wound.
Figure 9:
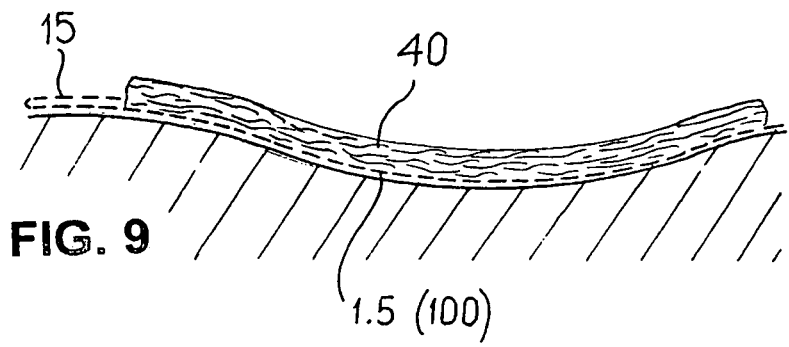
FIG. 9 shows an arrangement of a secondary dressing and wound distancing grid on a wound.

A wound distancing grid 1.5 shown in FIGS. 6 and 9 has a turned-back fold 15 that permits a simple removal of the wound distancing grid as well as of a secondary dressing 40 resting on it from the wound. In special instances turned-back fold 15 can have the same area as wound distancing grid 1.5.

Figure 7:
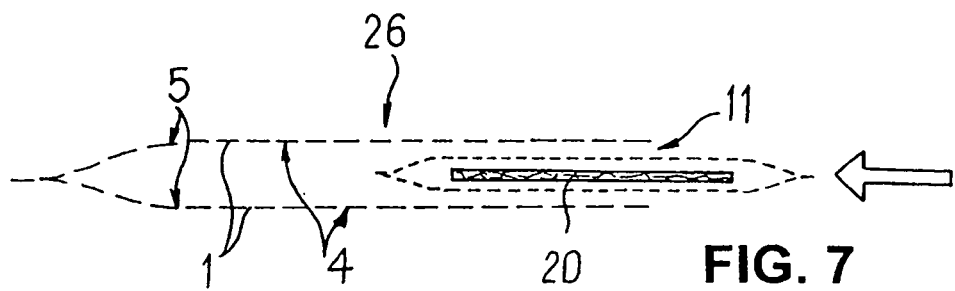
FIG. 7 shows an envelope produced from the material of the wound distancing grid in a schematic lateral view.

A deviating embodiment of the wound distancing grid is an envelope 26 made of the same material and that has an opening 11 for introducing and removing an encased absorption body 20 (cf. FIG. 7). Absorption body 20 is manufactured by the applicant under the trade name SORBION SACHET. This envelope 26 consists of two superposed material sections 1 welded to one another on their circumference with the exception of opening 11 (wound distancing grid). In the present case envelope 26 has two smooth surfaces 4 of which the one is directed toward the interior of the envelope and the second one is directed outward. Accordingly, envelope 26 has two rough surfaces 5 also facing toward the interior of the envelope and outward. In two further exemplary embodiments that are not shown the envelope has two identical surfaces 4 and 5 directed inward respectively outward.

Figure 8:
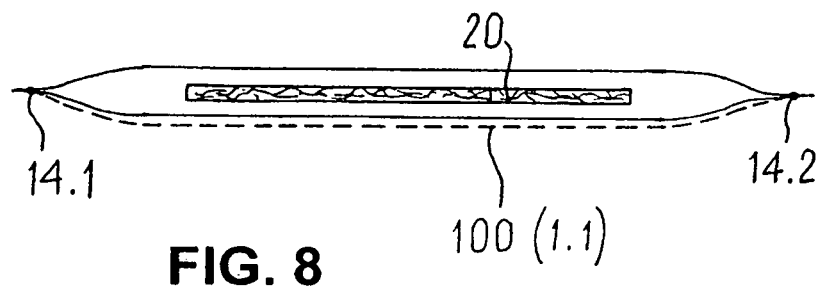
FIG. 8 shows the wound distancing grid adhered peripherally with a sachet, also in a schematic lateral view.

FIG. 8 shows wound distancing grid 1.1 fastened on encased absorption body 20. Wound distancing grid 1.1 is fastened by two welding seams 14.1, 14.2 located opposite one another. Welding seams 14.1, 14.2 are visible as points in FIG. 7.

Figure 11:
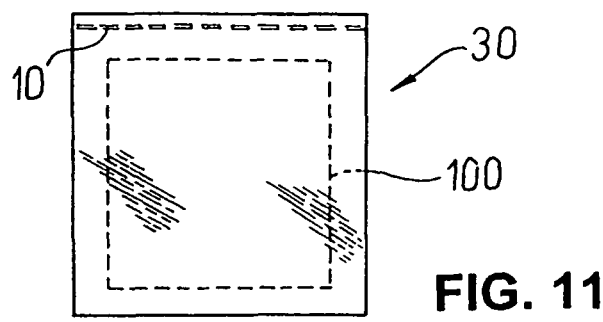
FIG. 11 shows a packaging bag with a wound distancing grid housed in it.

According to FIG. 11 the sterilized primary dressing 100 (wound distancing grid) is packed in a flat packaging bag 30 also sterilized with ethylene oxide. Packaging bag 30 is provided with a hermetic strip closure 10. Instead of the strip closure a marking line can be present if the packaging bag is welded together.

LIST OF REFERENCE NUMERALS 1 material section
2'; 2" perforations
3 wall
4; 5 surface
6 adhesive area
7 protective foil
8 edge
9 pull-off flap
10 strip closure
11 opening
12 section
13 periphery
14.1, 14.2 welded seam
15 turned-back fold
16 stamped line
17; 18 marking
20 absorption body
21 oblong hole
26 envelope
30 packaging bag
40 secondary dressing
100 primary dressing
A perforation axis (see 2)

The invention claimed is:

1. A liquid-permeable primary dressing (100) in the form of a flexible thermoplastic material section (1.1; 1.2; 1.3; 1.4; 1.5), comprising:
   a first surface (4) of the material section (1.1; 1.2; 1.3; 1.4; 1.5),
   a second surface (5) of the material section (1.1; 1.2; 1.3; 1.4; 1.5) facing away from the first surface (4),
   a plurality of three-dimensional perforations (2; 2"; 21) whose walls (3), starting from the first surface (4), run out into an edge projection with a free edge (8) and impart a rough grip to the second surface (5),
characterized in that at least one of the free edges (8) merges into a section (12) bent approximately vertically to a perforation axis (A), the first surface is smooth, and each free edge is substantially equidistant from the first surface.

2. The primary dressing according to claim 1, characterized in that the walls (3) of the perforations (2) are designed substantially conically.

3. The primary dressing according to claim 1, characterized in that the perforations (2) are small enough for a through meniscus formation of liquids with a specific weight between 0.9 and 1.2.

4. The primary dressing according to claim 1, characterized in that the perforations (2) are round or oval.

5. The primary dressing according to claim 1, characterized in that the perforations (2) are present in the form of oblong holes.

6. The primary dressing according to claim 1, characterized in that the perforations (2) are pyramid-shaped and that their walls (3) are segmented, i.e., separated from each other with stamped lines (16).

7. The primary dressing according to claim 4, characterized in that the round perforations (2) have a diameter of 650 to 800 μm.

8. The primary dressing according to claim 5, characterized in that the oblong holes are 900 to 1200 μm long with a width of approximately 700 μm.

9. The primary dressing according to claim 1, characterized in that the material section is smooth on its periphery (13) on its two sides, that is, on the first surface as well as on the second surface (4; 5) and that the second surface (5) that was first raw is thermally smoothed on the periphery (13).

10. The primary dressing according to claim 1, characterized in that markings (17; 18) are applied on the material section (1.4).

11. The primary dressing according to claim 1, characterized in that the material section (1.5) is provided with at least one turned-back fold (15).

12. The primary dressing according to claim 1, characterized in that the material section is connected to an encased absorption body (20).

13. The primary dressing according to claim 1, characterized in that the material section is formed to an envelope (26) into which an absorption body can be placed.

14. The primary dressing according to claim 1, characterized in that the material section is a carrier for pharmaceutical agents.

15. The use of the primary dressing according to claim 1 for covering wounds as a sterilized primary dressing (100) onto which absorbent secondary dressings (40) can be placed.

16. The use of the primary dressing according to claim 1 for one of the group consisting of compression therapy for chronic wounds and vacuum therapy.

17. A liquid-permeable wound care dressing having a flexible thermoplastic material section comprising:
  a first surface of the material section;
  a second surface of the material section facing away from the first surface; and
  a plurality of three-dimensional perforations passing into the first surface and having walls, that starting from the first surface, extend toward the second surface and into an edge projection with a free edge, and at least one free edge having a section that is bent substantially perpendicularly relative to a wall of the perforation, the bent section being capable of deflection relative to the respective free edge, wherein the edge projection and free edge impart a rough grip to the second surface, and wherein each free edge is substantially equidistant from the first surface.

18. A liquid-permeable wound care dressing having a flexible thermoplastic material section comprising:
  a first surface of the material section;
  a second surface of the material section facing away from the first surface; and
  a plurality of three-dimensional perforations passing into the first surface and having walls, that starting from the first surface, extend toward the second surface and into an edge projection with a free edge, and at least one free edge having a section that is bent substantially perpendicularly relative to a wall of the perforation, the bent section being capable of deflection relative to the respective free edge, wherein the edge projection and free edge impart a rough grip to the second surface, and wherein each free edge is substantially equidistant from the first surface;
  wherein the plurality of three-dimensional perforations each further comprise a first opening in the first surface and a second opening at the end of the walls extending toward the second surface.

* * * * *